United States Patent
Nagasawa et al.

[11] Patent Number: 6,121,301
[45] Date of Patent: Sep. 19, 2000

[54] SUBSTITUTED BENZOYLAMINOTHIAZOLE DERIVATIVES AND DRUGS CONTAINING THE SAME

[75] Inventors: Masaaki Nagasawa; Kenji Sato; Tadashi Kurimoto; Shigeru Ueki, all of Konan-machi, Japan

[73] Assignee: Zeria Pharmaceutical Co., Ltd., Tokyo, Japan

[21] Appl. No.: 09/284,477

[22] PCT Filed: Oct. 20, 1997

[86] PCT No.: PCT/JP97/03774

§ 371 Date: Apr. 21, 1999

§ 102(e) Date: Apr. 21, 1999

[87] PCT Pub. No.: WO98/17654

PCT Pub. Date: Apr. 30, 1998

[30] Foreign Application Priority Data

Oct. 24, 1996 [JP] Japan ................... 8-299266

[51] Int. Cl.[7] .................. C07D 277/56; A61K 31/425
[52] U.S. Cl. ............................ 514/365; 548/195
[58] Field of Search .............. 548/195; 514/365

[56] References Cited

U.S. PATENT DOCUMENTS

| | | |
|---|---|---|
| 4,829,073 | 5/1989 | Gidda et al. . |
| 5,075,301 | 12/1991 | Sasho et al. . |
| 5,510,478 | 4/1996 | Sabb .................... 548/183 |
| 5,712,270 | 1/1998 | Sabb .................... 548/183 |
| 5,981,557 | 9/1999 | Nagasawa ............ 514/365 |

FOREIGN PATENT DOCUMENTS

| | | |
|---|---|---|
| 1-313424 | 12/1989 | Japan . |
| 3-163074 | 7/1991 | Japan . |
| 4-279581 | 10/1992 | Japan . |

*Primary Examiner*—Robert Gerstl
*Attorney, Agent, or Firm*—Oblon, Spivak, McClelland, Maier & Neustadt, P.C.

[57] ABSTRACT

The present invention relates to a substituted benzoylaminothiazole derivative represented by the following formula (I):

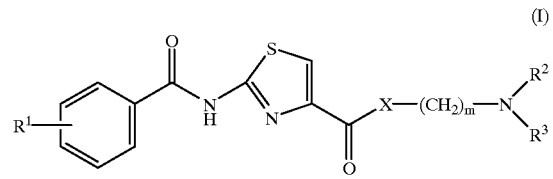

wherein X represents an imino group which may be substituted by a lower alkyl group, or an oxygen atom, $R^1$ represents a cyano group, a lower alkoxycarbonyl group, a lower alkoxycarbonylamino group, a lower alkylsulfonylamino group, a lower alkanoyl or lower alkylsulfonyl group which may be substituted by a halogen atom, a 1-ureido group, a halo-substituted lower alkyl group or a 2-pyrrolylimino group, $R^2$ and $R^3$ are the same or different and each independently represents a hydrogen atom or a lower alkyl group and m stands for an integer of 2 to 4, or a salt thereof; and a medicament comprising the compound as an effective ingredient. The compound of the invention is useful as a preventive and therapeutic agent for epigastric dyscomfort, nausea, vomiting, heartburn, anorexia, bellyache, abdominal flatulence, chronic gastritis or the like.

7 Claims, No Drawings

SUBSTITUTED BENZOYLAMINOTHIAZOLE DERIVATIVES AND DRUGS CONTAINING THE SAME

TECHNICAL FIELD

The present invention relates to a novel benzoylaminothiazole derivative having improving effects on the dysmotility in the gastrointestinal tract, a medicament containing the derivative and an intermediate for preparing said compound.

BACKGROUND ART

As a therapeutic agent for gastrointestinal dysmotility, dopamine antagonists such as domperidone and metoclopramide, opioate agonists such as trimebutine maleate, 5-$HT_3$ antagonists 5-$HT_4$ agonists such as cisapride, acetylcholine agonists such as acetylcholine chloride and the like have conventionally been provided for clinical use. In addition to them, a number of prokinetics have been studied with a view to treating gastrointestinal dysmotility (Japanese Patent Applications Laid-Open Nos. HEI 1-313424, HEI 3-163074 and HEI 4-279581).

These agents, however, do not always bring about sufficient effects for the improvement of dysmotility. There is a potential problem that side effects may possibly occur owing to the acting mechanism of the agent even if it has sufficient effects. So, the above-described agents are not completely satisfactory. Accordingly, there has been a demand for the development of a medicament having excellent improving effects on gastrointestinal dysmotility and having less side effects.

DISCLOSURE OF THE INVENTION

With the foregoing in view, the present inventors have carried out an extensive investigation. As a result, it has been found that a specific benzoylaminothiazole derivative has excellent improving effects on gastrointestinal dysmotility, has less side effects and is therefore useful as a medicament, leading to the completion of the present invention.

The present invention therefore provides a substituted benzoylaminothiazole derivative represented by the following formula (I):

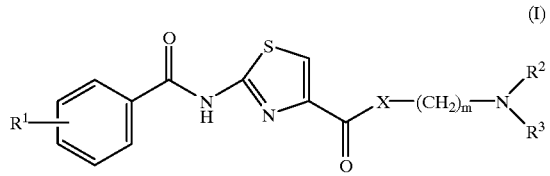

wherein X represents an imino group which may be substituted by a lower alkyl group, or an oxygen atom, $R^1$ represents a cyano group, a lower alkoxycarbonyl group, a lower alkoxycarbonylamino group, a lower alkylsulfonylamino group, a lower alkanoyl or lower alkylsulfonyl group which may be substituted by a halogen atom, a 1-ureido group, a halo-substituted lower alkyl group or a 2-pyrrolylimino group, $R^2$ and $R^3$ are the same or different and each independently represents a hydrogen atom or a lower alkyl group and m stands for an integer of 2 to 4; or a salt thereof.

The present invention also provides a medicament comprising as an effective ingredient the above-described substituted benzoylaminothiazole derivative (I) or salt thereof.

The present invention further provides a preventive and therapeutic agent for gastrointestinal dysmotility, which comprises as an effective ingredient the above-described substituted benzoylaminothiazole derivative (I) or salt thereof.

The present invention still further provides a preventive and therapeutic agent for epigastric dyscomfort, nausea, vomiting, heart burn, anorexia, bellyache, abdominal flatulence, chronic gastritis, reflux esophagitis, postgastrectomy syndrome or the like, which comprises as an effective ingredient the above-described substituted benzoylaminothiazole derivative (I) or salt thereof.

The present invention still further provides a pharmaceutical composition comprising the above-described substituted benzoylaminothiazole derivative (I) or salt thereof and a pharmaceutically acceptable carrier.

The present invention still further provides the use of the above-described substituted benzoylaminothiazole derivative (I) or salt thereof as a medicament.

The present invention still further provides a method for preventing or treating gastrointestinal dysmotility, which comprises administering an effective amount of the above-described substituted benzoylaminothiazole derivative (I) or salt thereof to mammals including human.

The present invention still further provides a thiazole derivative represented by the following formula (II):

wherein $R^1$ has the same meanings as described above, and Y represents a hydroxy or a lower alkoxy group or salt thereof which is useful as an intermediate for the preparation of the invention compound (I).

BEST MODES FOR CARRYING OUT THE INVENTION

The term "lower" as used herein means a linear, branched or cyclic carbon chain having 1 to 6 carbon atoms.

Accordingly, examples of the "lower alkyl group" of X, $R^2$ or $R^3$ and "lower alkyl potion" of $R^1$ in the above formula include linear, branched or cyclic alkyl groups having 1 to 6 carbon atoms such as methyl, ethyl, n-propyl, isopropyl, cyclopropyl, n-butyl, isobutyl, sec-butyl, tert-butyl, cyclobutyl, n-pentyl, 1-methylbutyl, 2-methylbutyl, isopentyl, tert-pentyl, 1,2-dimethylpropyl, neopentyl, 1-ethylpropyl, cyclopentyl, n-hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl and cyclohexyl. Among them, preferred lower alkyl groups are linear or branched $C_{1-4}$ alkyl groups.

Examples of the "lower alkoxy group" represented by Y and "lower alkoxy portion" of $R^1$ include linear, branched or cyclic alkoxy groups having 1 to 6 carbon atoms such as methoxy, ethoxy, n-propoxy, cyclopropoxy, isopropoxy, n-butoxy, isobutoxy, sec-butoxy, tert-butoxy, cyclobutoxy, n-pentyloxy, 1-methylbutoxy, 2-methylbutoxy, isopentyloxy, tert-pentyloxy, 1,2-dimethylpropoxy, neopentyloxy, 1-ethyl-propoxy, cyclopentyloxy, n-hexyloxy, 1-methylpentyloxy, 2-methylpentyloxy, 3-methylpentyloxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3- dimethylbutoxy, 1-methyl-1-ethylpropoxy, 1-ethyl-2-methylpropoxy, 1,1,2-trimethylpropoxy, 1,2,2-trimethylpropoxy and cyclohexyloxy. Among them, preferred are linear or branched $C_{1-4}$ alkoxy groups.

In $R^1$, the term "lower alkanoyl group" means linear, branched or cyclic $C_{2-7}$ alkanoyl groups, while the term "lower alkylsulfonyl group" means linear, branched or cyclic $C_{1-6}$ alkylsulfonyl groups. As the lower alkyl portion in the lower alkanoyl group or lower alkylsulfonyl group, those exemplified above as the "lower alkyl group" can be mentioned by way of example. Preferred examples of the alkanoyl group include acetyl, propionyl, butyryl and valeryl groups, while those of the alkylsulfonyl group include methylsulfonyl, ethylsulfonyl, propylsulfonyl, isopropylsulfonyl, butylsulfonyl, isobutylsulfonyl, sec-butylsulfonyl and tert-butylsulfonyl group.

In the present invention, the term "lower alkoxycarbonyl group" represented by $R^1$ means a linear, branched or cyclic $C_{2-7}$ alkoxycarbonyl group. The term "lower alkoxycarbonylamino group" means an amino group substituted by one linear, branched or cyclic $C_{2-7}$ alkoxycarbonyl group and examples include methoxycarbonylamino, ethoxycarbonylamino, propoxycarbonylamino, cyclopropoxycarbonylamino group, isopropoxycarbonylamino, butoxycarbonylamino, isobutoxycarbonylamino, sec-butoxycarbonylamino, tert-butoxycarbonylamino, cyclobutoxycarbonylamino, pentyloxycarbonylamino, 1-methylbutoxycarbonylamino, 2-methylbutoxycarbonylamino, isopentyloxycarbonylamino, tert-pentyloxycarbonylamino, 1,2-dimethylpropoxycarbonylamino, neopentyloxycarbonylamino, 1-ethylpropoxycarbonylamino, cyclopentyloxycarbonylamino, hexyloxycarbonylamino, 1-methylpentyloxycarbonylamino, 2-methylpentyloxycarbonylamino, 3-methylpentyloxycarbonylamino, isohexyloxycarbonylamino, 1-ethylbutoxycarbonylamino, 2-ethylbutoxycarbonylamino, 1,1-dimethylbutoxycarbonylamino, 1,2-dimethylbutoxycarbonylamino, 1,3-dimethylbutoxycarbonylamino, 2,2-dimethylbutoxycarbonylamino, 2,3-dimethylbutoxycarbonylamino, 3,3-dimethylbutoxycarbonylamino, 1-methylethylpropoxycarbonylamino, 1-methyl-2-methylpropoxycarbonylamino, 1,1,2-trimethylpropoxycarbonylamino, 1,2,2-trimethylpropoxycarbonylamino and cyclohexyloxycarbonylamino groups. The term "lower alkylsulfonylamino group" means an amino group substituted with one linear, branched or cyclic $C_{1-6}$ alkylsulfonyl group.

In the present invention, examples of the "halogen atom" include fluorine, chlorine, bromine and iodine atoms.

The term "halo-substituted lower alkyl group" represented by $R^1$ means a lower alkyl group substituted by at least one "halogen atom" exemplified above. Examples include fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 1-fluoroethyl, 2-fluoroethyl, 1,1-difluoroethyl, 1,2-difluoroethyl, 2,2-difluoroethyl, 1,1,2-trifluoroethyl, 1,2,2-trifluoroethyl, 2,2,2-trifluoroethyl, 1,1,2,2-tetrafluoroethyl, 1,2,2,2-tetrafluoroethyl, pentafluoroethyl, 1-chloroethyl, 2-chloroethyl, 1,1-dichloroethyl, 1,2-dichloroethyl, 2,2-dichloroethyl, 1,1,2-trichloroethyl, 1,2,2-trichloroethyl, 2,2,2-trichloroethyl, 1,1,2,2-tetrachloroethyl, 1,2,2,2-tetrachloroethyl, pentachloroethyl, 1-bromoethyl, 2-bromoethyl, 1,1-dibromoethyl, 1,2-dibromoethyl, 2,2-dibromoethyl, 1,1,2-tribromoethyl, 1,2,2-tribromoethyl, 2,2,2-tribromoethyl, 1,1,2,2-tetrabromoethyl, 1,2,2,2-tetrabromoethyl, pentabromoethyl, 1-iodoethyl, 2-iodoethyl, 1,1-diiodoethyl, 1,2-diiodoethyl, 2,2-diiodoethyl, 1,1,2-triiodoethyl, 1,2,2-triiodoethyl, 2,2,2-triiodoethyl, 1,1,2,2-tetraiodoethyl, 1,2,2,2-tetraiodoethyl, pentaiodoethyl, 1-fluoropropyl, 2-fluoropropyl, 3-fluoropropyl, 2,3-difluoropropyl, 3,3,3-trifluoropropyl, 2,2,3,3,3-pentafluoropropyl, heptafluoropropyl, 1-chloropropyl, 2-chloropropyl, 3-chloropropyl, 2,3-dichloropropyl, 3,3,3-trichloropropyl, 2,2,3,3,3-pentachloropropyl, heptachloropropyl, 1-bromopropyl, 2-bromopropyl, 3-bromopropyl, 2,3-dibromopropyl, 3,3,3-tribromopropyl, 2,2,3,3,3-pentabromopropyl, heptabromopropyl, 1-iodopropyl, 2-iodopropyl, 3-iodopropyl, 2,3-diiodopropyl, 3,3,3-triiodopropyl, 2,2,3,3,3-pentaiodopropyl and heptaiodopropyl groups, of which trifluoromethyl, trichloromethyl, tribromomethyl, 2,2,2-trifluoroethyl, 2,2,2-trichloroethyl and 2,2,2-tribromoethyl groups are particularly preferred.

As the invention compound (I), those having a cyano group as $R^1$ and a lower alkyl group as each of $R^2$ and $R^3$ is preferred.

The invention compound (I) or intermediate (II) for the preparation of the invention compound can be converted into its salt in a manner known per se in the art. Examples of the salt of the invention compound or intermediate include acid addition salts with an inorganic acid, such as hydrochloride, sulfate, nitrate, phosphate, hydrobromide and hydroiodide; and acid addition salts with an organic acid such as acetate, oxalate, malonate, succinate, hibenzate, maleate, fumarate, lactate, malate, citrate, tartrate, methanesulfonate and ethanesulfonate.

The present invention also embraces various solvates, such as hydrates, of the invention compound (I) or the intermediate (II) for the invention compound.

The invention compound (I) or the intermediate (II) for the invention compound can be prepared by various synthetic processes, with its basic skeleton or characteristics of its group taken into consideration. Typical synthetic processes (A and B) for it will be described below. Here, it is possible to prepare the invention compound by either one of the preparation process A and preparation process B, or a process in accordance therewith.

Preparation Process A:

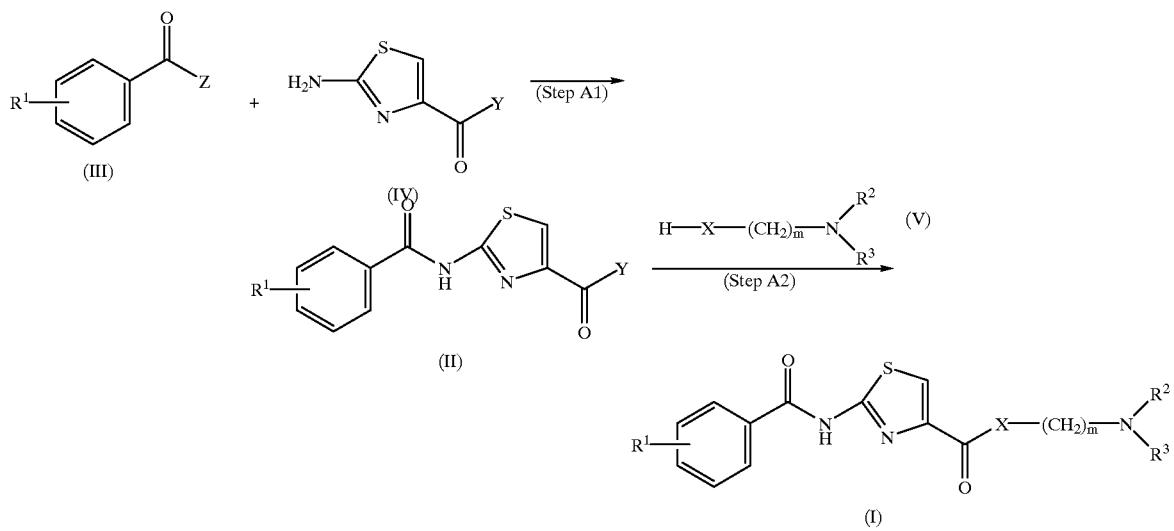

wherein Z represents an eliminating group such as p-nitrophenoxy group, a halogen atom or a hydroxy group, and $R^1$, $R^2$, $R^3$, X, Y and m have the same meanings as defined above.

This process will hereinafter be described by each step.

Step A1:

A thiazole derivative (II) can be prepared by reacting the compound represented by the formula (III) with the compound represented by the formula (IV). The reaction is carried out in t he presence or absence of a base, for example, an alkali metal carbonate such as potassium carbonate, potassium bicarbonate, sodium carbonate or sodium bicarbonate, an alkali metal hydroxide such as potassium hydroxide, sodium hydroxide or lithium hydroxide, an alkylamine such as triethylamine or diisopropylethylamine, or a pyridine or pyridine derivative such as lutidine or 4-dimethylaminopyridine, in a solventless manner or in a solvent inert to the reaction, for example, an aprotic polar solvent such as acetonitrile, N,N-dimethylformamide or dimethylsulfoxide, a halogen base solvent such as methylene chloride, chloroform or 1,2-dichloroethane, an ether base solvent such as ether, tetrahydrofuran or dioxane or a benzene base solvent such as toluene. The reaction can usually be carried out at room temperature or under heating.

When Z of Compound (III) represents a hydroxy group, the main reaction can be carried out using a condensing agent such as dicyclohexylcarbodiimide or carbonyldiimidazole or after converting Z into a highly reactive substituent such as p-nitrophenoxy group or halogen atom in a manner known per se in the art.

Incidentally, when the thiazole derivative (II) or invention compound (I) contains as $R^1$ an acyl group, it is preferred to prepare the thiazole derivative by protecting the acyl group of Compound (III) prior to the main reaction and then or after the reaction in the subsequent step A2, carrying out deprotection.

Step A2

The invention compound (I) can be obtained by reacting the thiazole derivative (II) obtained in the step A1 with Compound (V) and then, if necessary, subjecting the reaction mixture to N-alkylation reaction. The reaction is effected as in Step A1.

When Y of the thiazole derivative (II) represents a hydroxy group, it is also possible to carry out the main reaction by using a condensing agent such as dicyclohexylcarbodiimide or carbonyldiimidazole or after converting Y into a highly reactive substituent such as p-nitrophenoxy group or halogen atom in a manner known per se in the art.

The invention compound (I) can be introduced into another invention compound (I) by subjecting it to N-alkylation reaction. Examples of the N-alkylation reaction include methods known to date such as monoalkylation or dialkylation, more specifically, reaction using an alkyl halide.

As Compound (V), a commercially-available compound can be employed or alternatively, it can be prepared by using the above-described N-alkylation reactions in combination as needed.

Preparation Process B

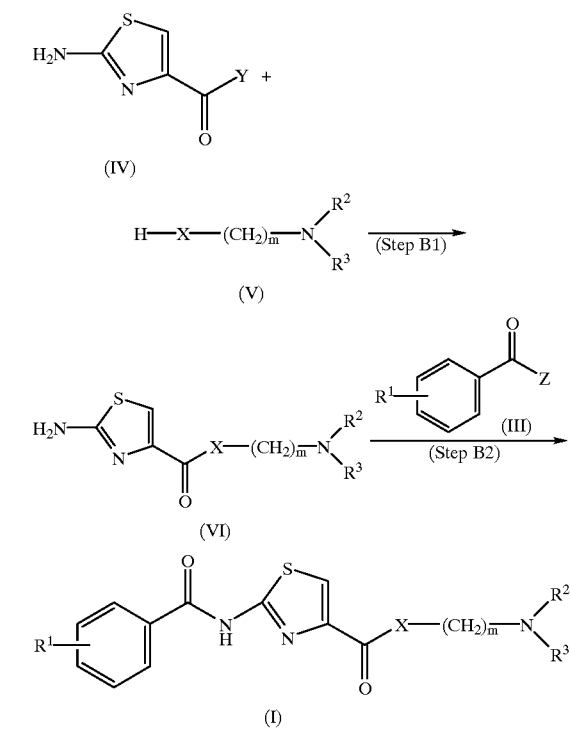

wherein $R^1$, $R^2$, $R^3$, X, Y, Z and m have the same meanings as described above.

Step B1

Compound (VI) can be prepared by reacting Compound (IV) with Compound (V). The reaction is effected in a similar manner to Step A2.

Step B2

Compound (VI) obtained in Step B1 can be introduced into the invention compound (I) by being reacted with Compound (III). The reaction is effected in a similar manner to Step A1.

Invention Compound (I) prepared by any one of the above-described Preparation Processes A and B and processes in accordance therewith can be converted into various salts in a manner known per se in the art.

Invention Compound (I) so obtained has, as will be described later, excellent improving effects on the dysmotility in the gastrointestinal tract and at the same time has high safety so that it is useful for the prevention and treatment of gastrointestinal dysmotility such as epigastric dyscomfort, nausea, vomiting, heart burn, anorexia, bellyache, abdominal flatulence, chronic gastritis, reflux esophagitis and postgastrectomy syndrome.

By being mixed with a pharmaceutically acceptable carrier, the invention compound (I) can be formed as a formulation for oral or parenteral administration. The invention compound (I) can be formulated into tablets, powders, granules or capsules by adding a suitable additive as needed, for example, an excipient such as lactose, mannitol, corn starch or crystalline cellulose, a binder such as cellulose derivative, gum arabic or gelatin, a disintegrator such as carboxymethylcellulose calcium or a lubricant such as talc or magnesium stearate. Such a solid formulationcanalsobe formed into an enteric-coated preparation by using a covering base such as hydroxypropyl methylcellulose phthalate, hydroxypropyl methylcellulose acetate succinate, cellulose acetate phthalate or methacrylate copolymer. As a formulation for parenteral administration, the invention compound can be formulated into a liquid agent for injection by using water, ethanol, glycerin or ordinarily-used surfactant, or into a suppository by using a suppository base in combination.

The dosage of the invention compound (I) varies depending on the age, weight, symptom, treatment effects, administration method and administration term. In the case of oral administration, it is preferred that the compound (I) is generally administered at a dose of 0.1 to 2,000 mg/day, particularly 1 to 300 mg/day in one to three portions a day.

EXAMPLES

The present invention will hereinafter be described more specifically by Referential Examples and Examples but it should however be borne in mind that the present invention is not limited to or by the following examples.

The preparation example of the intermediate (II) for preparing the invention compound (I) will be described below in Referential Example.

Referential Example 1

2-[N-(3-Cyanobenzoyl)amino]-4-(ethoxycarbonyl)-1,3-thiazole

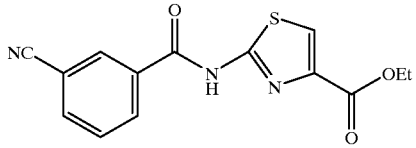

Step 1

In 10 ml of toluene, 576 mg of 3-cyanobenzoic acid were suspended, followed by the addition of 699 mg of thionyl chloride and 0.5 ml of N,N-dimethylformamide. The resulting mixture was stirred under heating at 80° C. for 5 hours. After cooling, the solvent was distilled off from the reaction mixture under reduced pressure. To the residue, n-hexane was added. The solvent was then distilled off, whereby 3-cyanobenzoyl chloride was obtained.

Step 2

In 15 ml of dried tetrahydrofuran, 968 mg of 2-amino-4-ethoxycarbonyl-1,3-thiazolehydrobromide were suspended. To the suspension, 1.19 g of triethylamine were added. A solution of 3-cyanobenzoyl chloride dissolved in 3 ml of dried tetrahydrofuran was added dropwise to the resulting mixture under ice cooling, followed by stirring at room temperature for 3 hours. Water was added to the reaction mixture and the resulting mixture was extracted with chloroform. The organic layer was then dried over magnesium sulfate. The solvent was then distilled off under reduced pressure. The residue was purified by chromatography on a silica gel column (chloroform: methanol=10:1), whereby 980 mg of 2-[N-(3-cyanobenzoyl)amino]-4-ethoxycarbonyl-1,3-thiazole were obtained as white crystals. Yield: 83%.

Melting point: 203.0 to 204.5° C.

Example 1

2-[N-(3-Cyanobenzoyl)amino]-4-[(2-diisopropylaminoethyl)aminocarbonyl]-1,3-thiazolehydrochloride

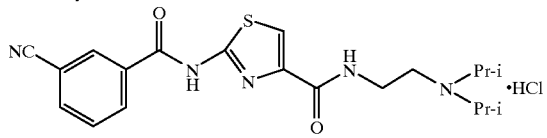

Step 1

In 1 liter of toluene, 200 g of 3-cyanobenzoic acid were suspended, followed by the addition of 128 ml of thionyl chloride and 1 ml of N,N-dimethylformamide. The resulting mixture was stirred under heating at 80° C. for 5 hours. After cooling of the reaction mixture, the solvent was distilled off under reduced pressure. To the residue, n-hexane was added. By distilling off the solvent under reduced pressure, 3-cyanobenzoyl chloride was obtained. The resulting 3-cyanobenzoyl chloride was dissolved in 3 liters of dried 1,2-dichloroethane, followed by the addition of 200 g of 2-amino-4-methoxycarbonyl-1,3-thiazole. The resulting mixture was heated under reflux for 5 hours. The reaction mixture was cooled. Crystals so precipitated were collected by filtration and then washed with water, whereby 289 g of 2-[N-(3-cyanobenzoyl)amino]-4-methoxycarbonyl-1,3-thiazole.hydrochloride were obtained. Yield: 80%.

Melting point: 201 to 205° C.

Step 2

Under an argon gas stream, 34.8 g of N,N-diisopropylethylenediamine and 620 ml of 1,2-dichloroethane were stirred under ice cooling. While maintaining the internal temperature of the reaction mixture at 15° C. or less, 138 ml of a toluene solution (2M) of trimethylaluminum were added dropwise and the resulting mixture was stirred at room temperature for 30 minutes. After stirring, the reaction mixture was cooled in ice bath and while maintaining the internal temperature at 20° C. or less, 2-[N-(3-cyanobenzoyl)amino]-4-methoxycarbonyl-1,3-thiazole.hydrochloride was added in portions. The resulting mixture was stirred at room temperature for 14 hours. The reaction mixture was poured into a mixture of 200 g of ice and 30 ml of concentrated hydrochloric acid, followed by stirring. The crystals precipitated were collected by suction filtration. The resulting crystals were washed successively with water and ether and then recrystallized from a mixed solvent of ethanol and water, whereby 101.1 g of the title compound were obtained as white crystals. Yield: 95.4%

Melting point: 160 to 163° C. MS (FAB) m/z: 400 (MH$^+$) IR (KBr) cm$^{-1}$: 3538, 3318, 2230, 1659, 1545; $^1$H-NMR (DMSO-d$_6$) δ: 1.30–1.36(12H,m), 3.15–3.20(2H,m), 3.60–3.70(4H,m), 7.75–7.81(1H,m), 7.98(1H,s), 8.11–8.13 (1H,m), 8.34–8.37(1H,m), 8.45(1H,brs), 8.52(1H,s), 9.75 (1H,brs), 13.00(1H,s).

Example 2

2-[(N-(4-Cyanobenzoyl)amino]-4-[(2-diisopropylaminoethyl)aminocarbonyl]-1,3-thiazole.hydrochloride

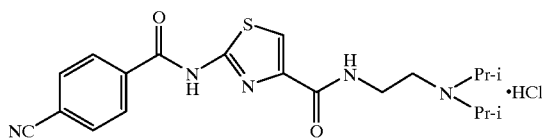

Step 1

To 25 g of 4-cyanobenzoic acid, 18.5 ml of thionyl chloride, 0.3 ml of N,N-dimethylformamide and 150 ml of toluene were added. The resulting mixture was stirred under heating at the internal temperature of 80° C. for 2.5 hours. After cooling of the reaction mixture, the solvent was distilled off under reduced pressure. To the residue, 28.2 g of 2-amino-4-methoxycarbonyl-1,3-thiazole and 500 ml of 1,2-dichloroethane were added, followed by heating under reflux for 3 hours. The reaction mixture was allowed to cool down and the crystals so precipitated were collected by filtration and washed with 0.5 N hydrochloric acid. The resulting crystals were suspended in 200 ml of ice water. To the resulting suspension, a 1N aqueous sodium hydroxide solution was added to adjust its pH to 8, followed by stirring for 30 minutes. The crystals so precipitated were collected by filtration, washed with water and then air dried, whereby 33.0 g of 2-[N-(4-cyanobenzoyl)amino]-4-methoxycarbonyl-1,3-thiazole were obtained. Yield: 67.5%;

Melting point: 228° C.

Step 2

To 1.00 g of 2-[N-(4-cyanobenzoyl)amino]-4-methoxycarbonyl-1,3-thiazole, 1.00 g of N,N-diisopropylethylenediamine and 5 ml of acetonitrile were added. The resulting mixture was heated under reflux for 8 hours. After the reaction mixture was allowed to cool down, 10 ml of 1N hydrochloric acid were added and the resulting mixture was stirred for 15 minutes. The crystals so precipitated were collected by filtration. The resulting crystals were recrystallized from ethanol, whereby 894 mg of the title compound were obtained as white crystals. Yield: 59%.

Melting point: 153 to 153.5° C. MS (FAB) m/z: 400 (MH$^+$); IR (KBr) cm$^{-1}$: 3426, 2232, 1671, 1642, 1551; $^1$H-NMR (DMSO-d$_6$) δ: 1.30–1.36(12H,m), 3.19(2H,brs), 3.60–3.70(4H,m), 7.98(1H,s), 8.03–8.06(2H,m), 8.20–8.23 (2H,m), 8.46(1H,brs), 9.79(1H,br), 13.08(1H,s).

Example 3

2-[N-(4-Acetylbenzoyl)amino]-4-[(2-diisopropylaminoethyl)aminocarbonyl]-1,3-thiazole.hydrochloride

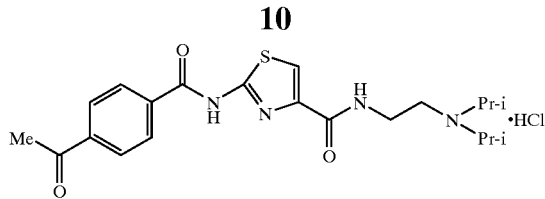

Step 1

In 7.54 g of 4-acetylbenzoic acid, 50 ml of methylene chloride and 8.0 ml of oxalyl chloride were added. The resulting mixture was stirred for 2 hours. The reaction mixture was concentrated under reduced pressure. To the residue, 6.58 g of p-nitrophenol and 100 ml of 1,2-dichloroethane were added, followed by heating under reflux for 2 hours. To the reaction mixture, 200 ml of chloroform were added. The resulting mixture was washed with a saturated aqueous solution of sodium bicarbonate, dried over anhydrous magnesium sulfate and distilled under reduced pressure to remove the solvent, whereby 13.58 g of 4-acetylbenzoic acid p-nitrophenyl ester were obtained. Yield: 100%.

$^1$H-NMR (CDCl$_3$) δ: 2.69(3H,s), 7.42–7.48(2H,m), 8.03–8.12(2H,m), 8.27–8.38(4H,m) MS (FAB) m/z: 286 (MH$^+$).

Step 2

To 831 mg of 4-acetylbenzoic acid p-nitrophenyl ester, 788 mg of 2-amino-4-[(2-diisopropylaminoethyl) aminocarbonyl]-1,3-thiazole were added. The resulting mixture was stirred at 130° C. for 8 hours. The reaction mixture was purified by column chromatography on NH silica gel (chloroform), whereby 693 mg of 2-[N-(4-acetylbenzoyl) amino]-4-[(2-diisopropylaminoethyl)aminocarbonyl]-1,3-thiazole were obtained. After 2 ml of a 4N hydrochloric acid—dioxane solution were added to the resulting compound, the solvent was distilled off under reduced pressure. The residue was recrystallized from a mixed solvent of isopropyl ether and ethanol, whereby 395 mg of the title compound were obtained as yellow powder.

Melting point: 163 to 169° C. (decomposed); MS (FAB) m/z: 417 (MH$^+$); IR (KBr) cm$^{-1}$: 1684, 1660, 1640, 1557; $^1$H-NMR (DMSO-d$_6$) δ: 1.27–1.35(12H,m), 2.66(3H,s), 3.08–3.24(2H,m), 3.59–3.78(4H,m), 7.97(1H,s), 8.09–8.12 (2H,m), 8.18–8.21(2H,m), 8.43–8.78(1H,m), 9.49–9.58(1H, m), 12.99(1H,s).

Compounds of Examples 4 to 19 were each obtained as described below in a similar manner to one of Examples 1 to 3.

Example 4

2-[N-[3-(1-Ureido)benzoyl]amino]-4-[(2-diisopropylaminoethyl)aminocarbonyl]-1,3-thiazole.hibenzate

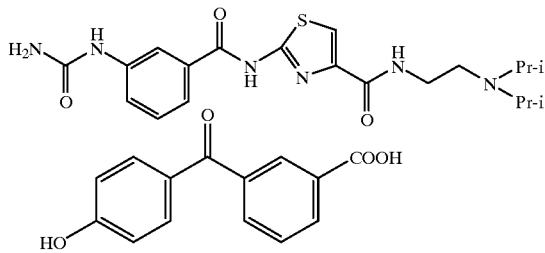

Melting point: 205 to 207° C. (decomposed); MS (FAB) m/z: 432 (MH$^+$); IR (KBr) cm$^{-1}$: 3250, 1650, 1551; $^1$H-NMR (DMSO-d$_6$) δ: 1.05–1.23(12H,m), 2.73(2H,brs), 3.10–3.80(7H,m), 6.78–6.83(2H,m), 7.26–7.29(1H,m), 7.38–7.44(1H,m), 7.48–7.67(6H,m), 7.83(1H,s), 7.95–7.96 (1H,m), 8.13(1H,brs), 8.33(1H,s), 10.06(1H,brs), 10.50(1H, br), 12.50(1H,br).

Example 5

2-[N-[3-(Methylsulfonylamino)benzoyl]amino]-4-[(2-diisopropylaminoethyl)aminocarbonyl]-1,3-thiazole.oxalate

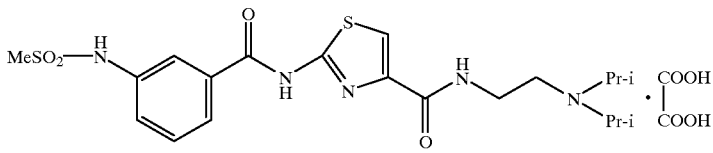

Melting point: 164.5 to 166° C. MS (FAB) m/z: 468 (MH⁺); IR (KBr) cm⁻¹: 3270, 1650, 1557, 1321, 1300; ¹H-NMR (DMSO-d₆) δ: 1.22–1.27(12H,m), 3.09(3H,s), 3.00–3.10(2H,m), 3.50–3.80(8H,m), 7.41–7.55(2H,m), 7.81–7.84(1H,m), 7.91(1H,s), 8.41(1H,brs), 10.07(1H,brs).

Example 6

2-[N-(3-trifluoromethylbenzoyl)amino]-4-[(2-diisopropylaminoethyl)aminocarbonyl]-1,3-thiazole

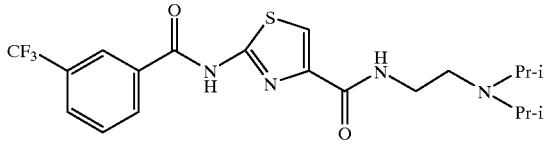

Melting point: 160 to 160.5° C. MS (FAB) m/z: 443 (MH⁺); IR (KBr) cm⁻¹: 3354, 2968, 1668, 1640, 1495; ¹H-NMR (DMSO-d₆) δ: 1.02–1.12(12H,m), 2.63(2H,brs), 3.08(4H,brs), 7.76–7.82(4H,m), 8.35–8.46(2H,m), 12.50 (1H,br).

Example 7

2-[N-[4-(1-Ureido)benzoyl]amino]-4-[(2-diisopropylaminoethyl)aminocarbonyl]-1,3-thiazole.hydrochloride

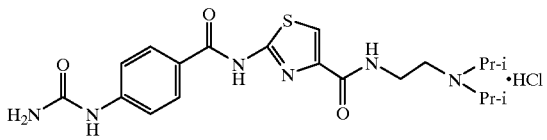

Melting point: 208 to 209° C. MS (FAB) m/z: 433 (MH⁺); IR (KBr) cm⁻¹: 3250, 2685, 1696, 1628, 1522; ¹H-NMR (DMSO-d₆) δ: 1.30–1.35(12H,m), 3.17(2H,brs), 3.64–3.69 (4H,m), 6.11(2H,brs), 7.55–7.68(2H,m), 7.89(1H,s), 8.00–8.06(2H,m), 8.45–8.49(1H,m), 9.10(1H,s), 9.59(1H, brs), 12.54(1H,brs).

Example 8

2-[N-(4-Methylsulfonylbenzoyl)amino]-4-[(2-diisopropylaminoethyl)aminocarbonyl]-1,3-thiazole.½ oxalate

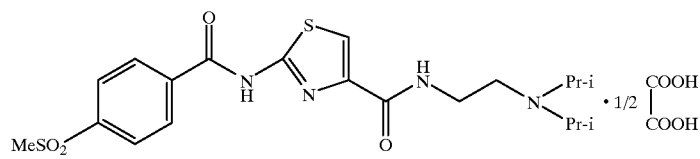

Melting point: 250 to 251° C. MS (FAB) m/z: 453 (MH⁺); IR (KBr) cm⁻¹: 3250, 1664, 1559, 1313, 1300, 1152; ¹H-NMR (DMSO-d₆) δ: 1.15–1.78(12H,m), 2.91(2H,brs), 3.20–3.80(7H,m), 3.29(3H,s), 7.87(1H,s), 8.07–8.10(2H,m), 8.28–8.32(2H,m).

Example 9

2-[N-(4-Trifluoroacetylbenzoyl)amino]-4-[(2-diisopropylaminoethyl)aminocarbonyl]-1,3-thiazole.hydrochloride

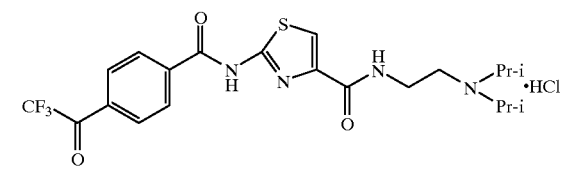

Melting point: 153 to 154° C. MS (FAB) m/z: 471 (MH⁺); IR (KBr) cm⁻¹: 3283, 1655, 1636, 1547; ¹H-NMR (DMSO-d₆) δ: 1.30–1.36(12H,m), 3.17–3.20(2H,m), 3.60–3.70(4H, m), 7.76–7.80(2H,m), 7.94(1H,s), 8.12–8.16(2H,m), 8.52 (1H,brs), 9.79(1H,brs), 12.89(1H,s).

Example 10

2-[N-(4-(Methoxycarbonylamino)benzoyl]amino]-4-[(2-diisopropylaminoethyl)aminocarbonyl]-1,3-thiazole.hydrohloride

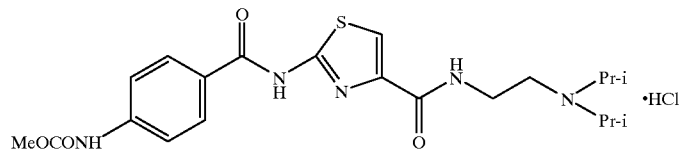

Melting point: 250° C. (decomposed); MS (FAB) m/z: 448 (MH$^+$); IR (KBr) cm$^{-1}$: 3750, 1736, 1655, 1609, 1597; $^1$H-NMR (DMSO-d$_6$) δ: 1.30–1.36(12H,m), 3.19(2H,brs), 3.64–3.71(4H,m), 3.71(3H,s), 7.60–7.64(2H,m), 7.91(1H,s), 8.03–8.07(2H,m), 8.41(1H,brs), 9.67(1H,brs), 10.10(1H,s), 12.59(1H,s).

Example 11
2-[N-[3-(2-Pyrrolylimino)benzoyl]amino]-4-[(2-diisopropylaminoethyl)aminocarbonyl]-1,3-thiazole.2 hibenzate

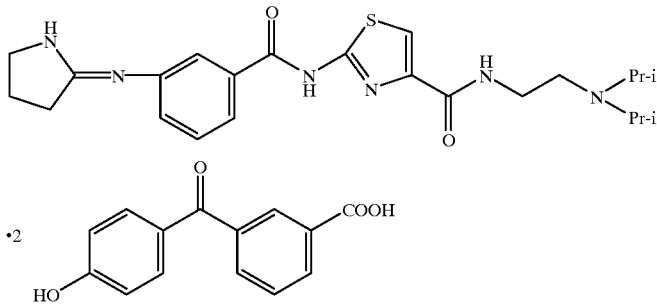

Melting point: 160 to 162° C. MS (FAB) m/z: 457 (MH$^+$); IR (KBr) cm$^{-1}$: 3000, 1650, 1580, 1550; $^1$H-NMR (DMSO-d$_6$) δ: 0.95–1.10(12H,m), 1.90–1.99(2H,m), 2.50–2.70(4H,m), 3.00–3.06(2H,m), 3.20–3.95(8H,m), 6.79–6.82(4H,m), 7.28–7.32(2H,m), 7.38–7.68(13H,m), 7.79(1H,s), 7.90–7.96(3H,m), 8.10(1H,brs).

Example 12
2-[N-[3-(Methoxycarbonylamino)benzoyl]amino]-4-[(2-diisopropylaminoethyl)aminocarbonyl]-1,3-thiazole.hydrochloride

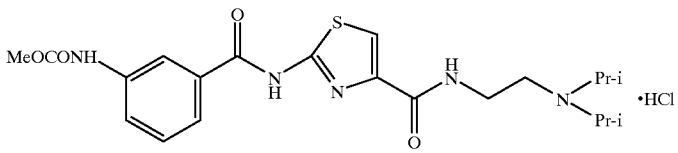

Melting point: 142 to 144° C. MS (FAB) m/z: 448 (MH$^+$); IR (KBr) cm$^{-1}$: 3250, 2664, 1734, 1660, 1550; $^1$H-NMR (DMSO-d$_6$) δ: 1.30–1.35(12H,m), 3.10–3.20(2H,m), 3.60–3.70(4H,m), 3.70(3H,s), 7.43–7.49(1H,m), 7.68–7.74(2H,m), 7.93(1H,s), 8.14(1H,s), 8.42(1H,brs), 9.50(1H,brs), 9.91(1H,s), 12.71(1H,s).

Example 13
2-[(N-(3-acetylbenzoyl)amino]-4-[(2-diisopropylaminoethyl)aminocarbonyl]-1,3-thiazole.hydrochloride

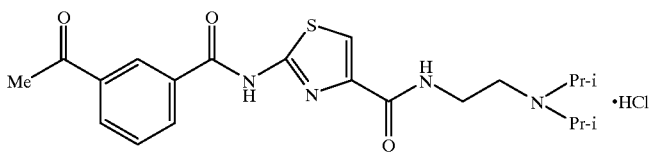

Melting point: 211 to 215° C. MS (FAB) m/z: 417 (MH$^+$); IR (KBr) cm$^{-1}$: 1680, 1670, 1554; $^1$H-NMR (DMSO-d$_6$) δ: 1.30–1.37(12H,m), 2.68(3H,s), 3.13–3.21(2H,m), 3.58–3.64(8H,m), 7.73(1H,t), 7.97(1H,s), 8.18–8.22(1H,m), 8.29–8.33(1H,m), 8.51(1H,t), 8.67–8.68(1H,m), 9.93–10.08(1H,m), 12.47–12.58(1H,m).

Example 14
2-[(N-(3-Cyanobenzoyl)amino]-4-[(3-diisopropylaminopropyl)aminocarbonyl]-1,3-thiazole

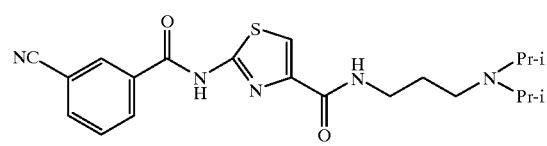

MS (FAB) m/z: 414 (MH$^+$); IR (KBr) cm$^{-1}$: 2361, 1653, 1558; $^1$H-NMR (CDCl$_3$) δ: 1.09(12H,d), 1.75–1.80(2H,m), 2.67–2.72(2H,m), 3.12–3.19(2H,m), 3.46–3.53(2H,m), 7.65–7.72(2H,m), 7.86–7.93(2H,m), 8.32–8.39(2H,m), 11.50–12.00(1H,m).

Example 15
2-[N-(4-Cyanobenzoyl)amino]-4-[(3-diisopropylaminopropyl)aminocarbonyl]-1,3-thiazole

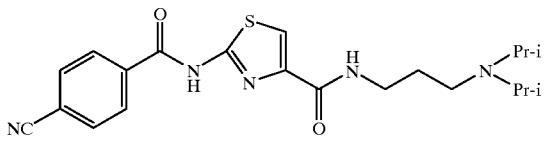

MS (FAB) m/z: 414 (MH⁺); IR (KBr) cm$^{-1}$: 2228, 1646, 1553; $^1$H-NMR (CDCl$_3$) δ: 1.07–1.16(12H,m), 1.79–1.84 (2H,m), 2.77–2.82(2H,m), 3.18–3.28(2H,m), 3.44–3.51(2H, m), 5.10–5.50(1H,m), 7.67(1H,s), 7.81–7.84(2H,m), 7.96–8.04(1H,m), 8.27–8.30(2H,m)

Example 16

2-[N-(3-Cyanobenzoyl)amino]-4-[(2-isopropylaminoethyl) aminocarbonyl]-1,3-thiazole.dihydrochloride

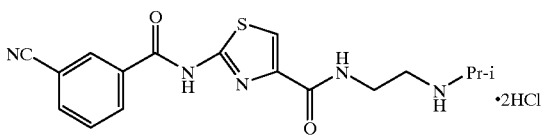

Melting point: 225 to 229° C. (decomposed); MS (FAB) m/z: 358 (MH⁺); IR (KBr) cm$^{-1}$: 1698, 1667; $^1$H-NMR (DMSO-d$_6$) δ: 1.24–1.27(6H,m), 3.02–3.16(2H,m), 3.28–3.36(1H,m), 3.57–3.68(2H,m), 7.78(1H,t), 8.02(1H,s), 8.10–8.14(1H,m), 8.29–8.38(2H,m), 8.53(1H,s), 8.80–9.16 (3H,m), 12.95–13.08(1H,m).

Example 17

2-[N-(4-Cyanobenzoyl)amino]-4-[(2-isopropylaminoethyl) aminocarbonyl]-1,3-thiazole

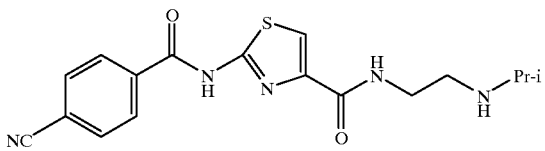

Melting point: 198° C. (decomposed); MS (FAB) m/z: 358 (MH⁺); IR (KBr) cm$^{-1}$: 3402, 2980, 2232, 1671, 1647, 1551; $^1$H-NMR (DMSO-d$_6$) δ: 1.24(6H,d), 3.08–3.18(2H, m), 3.28–3.45(1H,m), 3.60–3.64(2H,m), 8.00(1H,s), 8.02–8.08(2H,m), 8.20–8.25(2H,m), 8.26–8.33(1H,m).

Example 18

2-[N-(4-Cyanobenzoyl)amino]-4-[(2-diisopropylaminoethoxy)carbonyl]-1,3-thiazole

Step 1

To 1 g of 2-[N-(4-cyanobenzoyl)amino-4-methoxycarbonyl-1,3-thiazole obtained in the step 1 of Example 2, 1.98 g of potassium carbonate, 24 ml of methanol and 6 ml of water were added. The resulting mixture was stirred at 70 to 80° C. for 6 hours. The reaction mixture was concentrated under reduced pressure. Water was added to the concentrate, followed by washing with chloroform. To the water layer, 1N hydrochloric acid was added under ice cooling to adjust the pH to 5. The crystals so precipitated were collected by filtration, whereby 456 mg of 2-[N-(4-cyanobenzoyl)amino]-4-hydroxycarbonyl-1,3-thiazole were obtained.

Step 2

To 450 mg of 2-[N-(4-cyanobenzoyl)amino]-4-hydroxycarbonyl-1,3-thiazole, 10 ml of anhydrous methylene chloride were added. Under an argon gas atmosphere, 803 mg of 1,1'-carbonyldiimidazole were added and the resulting mixture was stirred for one hour. To the reaction mixture, 720 mg of 2-diisopropylaminoethanol were added and the resulting mixture was stirred for 1.5 hours. Chloroform was added to the reaction mixture. The resulting mixture was washed successively with water, a saturated aqueous solution of sodium bicarbonate and saturated saline, dried over anhydrous sodium sulfate and then distilled under reduced pressure to remove the solvent. The residue was purified by chromatography on a silica gel column (chloroform:methanol=9:1). To the resulting solid, diisopropyl ether was added, followed by trituration, whereby 528 mg of the title compound were obtained as a colorless solid.

Yield: 80%. Melting point: 152 to 153° C. MS (FAB) m/z: 401 (MH⁺); IR (KBr) cm$^{-1}$: 2969, 2230, 1725, 1673, 1545; $^1$H-NMR (CDCl$_3$) δ: 1.01(6H,d), 2.71(2H,t), 2.94–3.07(2H, m), 4.14(2H,t), 7.79–7.83(2H,m), 7.91(1H,s), 7.99–8.03 (2H,m).

Example 19

2-[N-(4-Methoxycarbonylbenzoyl)amino]-4-[(2-diisopropylaminoethyl)aminocarbonyl]-1,3-thiazole.½ fumarate

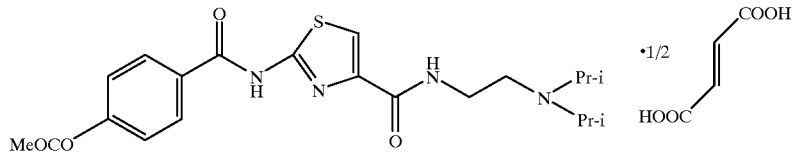

Melting point: 221 to 221.5° C. MS (FAB) m/z: 432 (MH$^+$); IR (KBr) cm$^{-1}$: 3112, 1725, 1661, 1538; $^1$H-NMR (DMSO-d$_6$) δ: 1.03–1.09(6H,m), 2.60–2.70(2H,m), 3.00–4.20(12H,m), 3.90(3H,s), 6.59(1H,s), 7.81(1H,s), 8.00–8.02(1H,m), 8.08–8.12(2H,m), 8.15–8.21(2H,m).

Formulation Example 1

| Compound of Example 1 | 20 g |
|---|---|
| Lactose | 315 g |
| Corn starch | 125 g |
| Crystalline cellulose | 25 g |

The above-described ingredients were uniformly mixed, followed by the addition of 200 ml of a 7.5% aqueous hydroxypropylcellulose solution. The resulting mixture was pulverized into granules through a screen of 0.5 mm in diameter by an extruder. Immediately after that, the resultant granules were rounded by Marumerizer and then dried, whereby granules were obtained.

Formulation Example 2

| Compound of Example 2 | 20 g |
|---|---|
| Lactose | 100 g |
| Corn starch | 36 g |
| Crystalline cellulose | 30 g |
| Carboxymethylcellulose calcium | 10 g |
| Magnesium stearate | 4 g |

The above-described ingredients were uniformly mixed. The resulting mixture was pressed into 200 mg tablets by a punch of 7.5 mm in diameter on a single punch tableting machine.

Formulation Example 3

| Compound of Example 10 | 100 mg |
|---|---|
| Sodium acetate | 2 mg |
| Acetic acid (for adjusting pH to 5.8) | q.s. |
| Distilled water | q.s. |
| Total | 10 ml/vial |

According to the above formulation, an injection was prepared in a manner known per se in the art.

Test 1

Gastroprokinetic activity

Force transducers (F-12IS; manufactured by Star Medical) were chronically implanted onto the gastric antrum and duodenum in dogs (weight: 9 to 10 kg) [Itoh, Z. et al., Am. J. Dig. Dis., 22, 17–124(1977)]. The test was carried out two hours after feeding (30 g/kg, Gaines meal; product of Ajinomoto General Foods). Contraction signals obtained from each transducer were amplified (RTA-1200; manufactured by Nihon Kohden) and recorded on a recorder and a computer.

The area under the contraction wave and base line in the antrum was integrated by an analysis program (DSSFFT, V. 21; manufactured by Nihon Kohden). Motor activity in the antrum was expressed as the motor index. The test compound was dissolved in physiological saline and administered intravenously.

The results were calculated by the following equation and are shown in Table 1 as % of motor index.

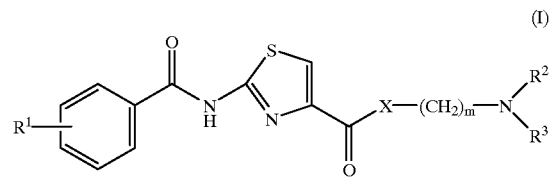

TABLE 1

| Test Compound | Dose (mg/kg) | Motor index (%) |
|---|---|---|
| Compound of Ex. 1 | 1 | 228 |
| Compound of Ex. 2 | 1 | 245 |
| Compound of Ex. 3 | 1 | 145 |
| Compound of Ex. 13 | 1 | 145 |

Test 2

Toxicity Test

Three ICR mice (4–5 weeks) were employed in each group. Test compound suspended with 5% gum arabic was given orally at a dose of 500 mg/kg. Within one week observation, no case of death was observed in each group.

CAPABILITY OF EXPLOITATION IN INDUSTRY

The compound according to the present invention markedly enhances gastrointestinal motility, thereby alleviating digestive dysmotility and at the same time, exhibits high safety so that it is useful for the prevention and treatment of various gastrointestinal dysmotility.

What is claimed is:

1. A substituted benzoylaminothiazole derivative represented by the following formula (I):

wherein X represents an imino group which may be substituted by a lower alkyl group or an oxygen atom, R$^1$ represents a cyano group, a lower alkoxycarbonyl group, a lower alkoxycarbonylamino group, a lower alkylsulfonylamino group, a lower alkanoyl or lower alkylsulfonyl group which may be substituted by a halogen atom, a 1-ureido group or a 2-pyrrolylimino group, R$^2$ and R$^3$ are the same or different and each independently represents a hydrogen atom or a lower alkyl group and m stands for an integer of 2 to 4; or a salt thereof.

2. The substituted benzoylaminothiazole derivative or salt thereof according to claim 1, wherein in the formula (I), R$^1$ represents a cyano group and R$^2$ and R$^3$ each independently represents a lower alkyl group.

3. A pharmaceutical composition comprising the substituted benzoylaminothiazole derivative or salt thereof as claimed in claim 1 and a pharmaceutically acceptable carrier.

4. The pharmaceutical composition according to claim 3, which is a preventive and therapeutic agent for epigastric dyscomfort, nausea, vomiting, heart burn, anorexia, bellyache, abdominal flatulence, chronic gastritis, reflux esophagitis or postgastrectomy syndrome.

5. The pharmaceutical composition according to claim 4, which is a preventive and therapeutic agent for gastrointestinal dysmotility.

6. A method for preventing and treating gastrointestinal dysmotility, which comprises administering an effective amount of the substituted benzoylaminothiazole derivative or salt thereof as claimed in claim 1 to mammals including human.

7. A thiazole derivative represented by the following formula (II):

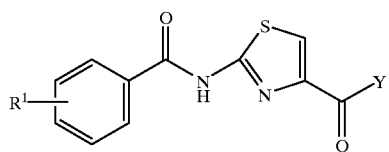
(II)

wherein $R^1$ represents a cyano group, a lower alkoxycarbonyl group, a lower alkoxycarbonylamino group, a lower alkylsulfonylamino group, a lower alkanoyl or lower alkylsulfonyl group which may be substituted by a halogen atom, a 1-ureido group or a 2-pyrrolylimino group and Y represents a hydroxy or lower alkoxy group, or salt thereof.

* * * * *

UNITED STATES PATENT AND TRADEMARK OFFICE
CERTIFICATE OF CORRECTION

PATENT NO. : 6,121,301  
DATED : September 19, 2000  
INVENTOR(S) : Masaaki Nagasawa, et al.

It is certified that error appears in the above-identified patent and that said Letters Patent is hereby corrected as shown below:

<u>Column 19,</u>
Line 6, Claim 5 "according to claim 4" should be --according to claim 3--

Signed and Sealed this

Twelfth Day of June, 2001

*Attest:*

*Nicholas P. Godici*

*Attesting Officer*

NICHOLAS P. GODICI
*Acting Director of the United States Patent and Trademark Office*